(12) United States Patent
Dracker

(10) Patent No.: US 10,190,092 B2
(45) Date of Patent: Jan. 29, 2019

(54) PROCUREMENT OF PLACENTAL STEM CELLS

(71) Applicant: Robert A. Dracker, Liverpool, NY (US)

(72) Inventor: Robert A. Dracker, Liverpool, NY (US)

(*) Notice: Subject to any disclaimer, the term of this patent is extended or adjusted under 35 U.S.C. 154(b) by 571 days.

(21) Appl. No.: 14/146,278

(22) Filed: Jan. 2, 2014

(65) Prior Publication Data

US 2014/0113369 A1  Apr. 24, 2014

Related U.S. Application Data

(63) Continuation-in-part of application No. 13/753,971, filed on Jan. 30, 2013, now abandoned, and a continuation-in-part of application No. 13/584,135, filed on Aug. 13, 2012, now abandoned.

(60) Provisional application No. 61/522,287, filed on Aug. 11, 2011.

(51) Int. Cl.
*C12N 5/073* (2010.01)

(52) U.S. Cl.
CPC .................... *C12N 5/0605* (2013.01)

(58) Field of Classification Search
None
See application file for complete search history.

(56) References Cited

U.S. PATENT DOCUMENTS

| | | | |
|---|---|---|---|
| 7,045,148 B2 | 5/2006 | Hariri | |
| 2005/0176139 A1 | 8/2005 | Chen et al. | |
| 2006/0060494 A1* | 3/2006 | Goodman | A61B 5/14 206/570 |
| 2007/0134210 A1 | 6/2007 | Heidaran | |
| 2007/0190042 A1 | 8/2007 | Edinger et al. | |
| 2007/0190649 A1 | 8/2007 | Gage | |
| 2008/0050814 A1* | 2/2008 | Allickson | A01N 1/02 435/366 |
| 2008/0064098 A1 | 3/2008 | Allickson | |
| 2008/0152629 A1 | 6/2008 | Edinger et al. | |
| 2009/0123437 A1 | 5/2009 | Takebe | |
| 2009/0136471 A1 | 5/2009 | Heidaran et al. | |
| 2010/0248206 A1 | 9/2010 | Kuypers et al. | |
| 2010/0291679 A1 | 11/2010 | Edinger et al. | |
| 2010/0323446 A1 | 12/2010 | Barnett et al. | |
| 2012/0177616 A1 | 7/2012 | Serikov et al. | |

FOREIGN PATENT DOCUMENTS

WO    2008156659    12/2008

OTHER PUBLICATIONS

Streptomycin, PubChem Entry, 2016.*

Sadowski et al., Intrarenal Vasodilator Systems: No, Prostaglandins and Bradykinin. An Integrative Approach, Journal of Physiology and Pharmacology 2008, 59, Suppl 9, 105-119.*
Vladimir Serikov, Catherine Hounshell, Sandra Larkin, William Green, Hirokazu Ikeda, Mark C. Waters and Frans A. Kuypers, A Bried Communication: Human Term Placenta as a Source of Hematopoietic Cells, Experimental Biology and Medicine 2009, 234:813-823, doi 10.3181/0809-BC-262.
International Search Report Form PCT/ISA/220, International Application No. PCT/US2012/050580, pp. 1-11, dated Feb. 20, 2013.
PBS_Buffer, PBS buffer recipe, 2010.
Tobramcyin, Tobramycin product sheet, Sigma Aldrich, 2013.
Isotonic, Isotonic definition, Dictionary definition, 2013.
Blood Osmolarity, Medline Plus definition, 2013.
Hyclone-Media. ThermoScientific Cell Media Product Manual, 2010.
Citric-acid-antioxidant, Citric acid properties, 2005.
Papaverine, Chandra et al, An opium alkaloid—papaverine ameliorates ethanol-induced hepatotoxicity, Indian Joui biochem., 2000. 15(2), 155-160.
Bertheussen. Growth of cells in a new defined protein-free medium, Cytotechnology 11:219-231. 1993.
Brazel, Glutamate enhances survival and proliferation of neural progenitors derived from the subventricular zone, Neuroscience, 131, 2005.
Neurobasal, Gibco cell culture media product sheet, 2006.
Tsagias, Nikos, et al., 'Placenta perfusion has hematopoietic and mesenchymal progenitor stem cell potential', Transfusion, May 2011, vol. 51 No. 5, pp. 976-985, see p. 977.
M.J.R. Ragaller, H. Theilen and T. Koch, "Volume replacement in critically ill patients with acute renal failure", Journal of the American Society of Nephrology, 2001, vol. 12, S33-S39.

(Continued)

*Primary Examiner* — Taeyoon Kim
*Assistant Examiner* — Srikanth Patury
(74) *Attorney, Agent, or Firm* — Bond Schoeneck & King, PLLC; George R. McGuire; Blaine Bettinger

(57) ABSTRACT

Methods and solutions for the preservation and procurement of placental stem cells. A method for collecting stem cells from a placenta includes draining cord blood from the placenta and collecting the drained cord blood in a first collection. The drained placenta is perfused with a first perfusion solution including a placental preservative base solution and a vasodilator. The placenta is perfused with a second perfusion solution including placental preservative base solution, a stem cell releasing agent, an antibiotic, and an anticoagulant, and a predetermined amount of time is allowed to elapse as the first and second perfusion solutions perfuse the placenta. The first and second perfusion solutions, which contain stem cells from the placenta, are then collected in a second collection.

14 Claims, 2 Drawing Sheets

(56) References Cited

OTHER PUBLICATIONS

Figure 1:
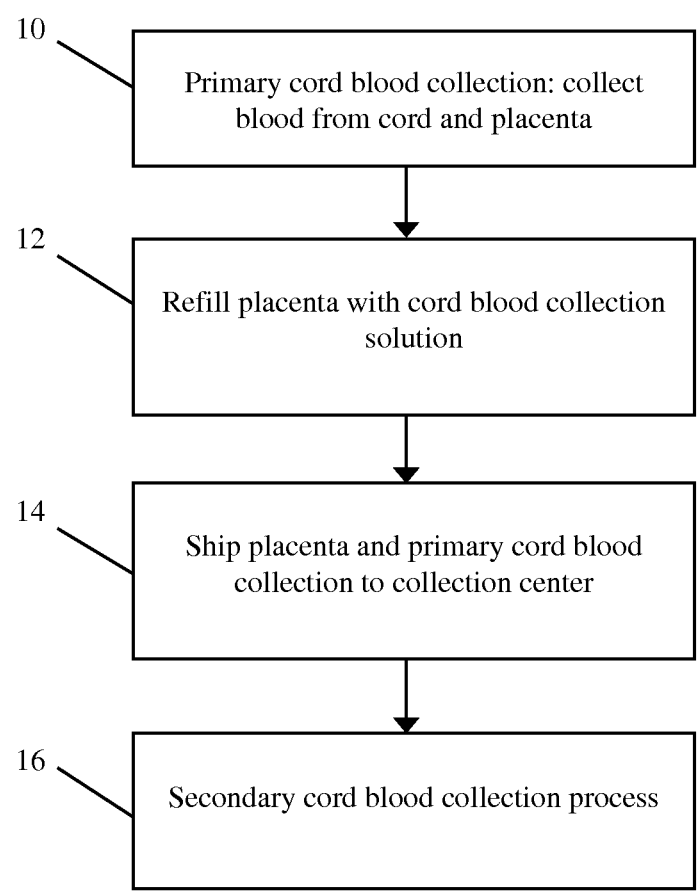

G. Di, J. Wang, M. Liu, C.-T. Wu, Y. Han and H. Duan, "Development and Evaluation of a Trehalose-Contained Solution Formula to Preserve hUC-MSCs at 4° C.", Journal of Cellular Physiology 2012, vol. 227, pp. 879-884.
International Search Report Form PCT/ISA/210, International Application No. PCT/US2013/023868, pp. 1-13, dated Jun. 21, 2013.

* cited by examiner

PROCUREMENT OF PLACENTAL STEM CELLS

CROSS-REFERENCE TO RELATED APPLICATIONS

This application is a continuation-in-part of U.S. patent application Ser. No. 13/584,135, filed on Aug. 13, 2012 and entitled "Procurement of Placental Stem Cells," which claims priority to U.S. Provisional Patent Application Ser. No. 61/522,287, filed on Aug. 11, 2011, and a continuation-in-part of U.S. patent application Ser. No. 13/753,971, filed on Jan. 30, 2013 and entitled "Procurement of Placental Stem Cells and Umbilical Cord Segments," the entire disclosures of which are incorporated herein by reference.

BACKGROUND OF THE INVENTION

1. Field of the Invention

The present invention relates to placental stem cells and, more specifically, to a method for the procurement of placental stem cells.

2. Description of the Related Art

Stem cells are master cells found in all multicellular organisms. These special cells are important to the human body, for example, because they are capable of: (i) differentiating into a multitude of different specialized cell types; and (ii) dividing to maintain a supply of stem cells. In humans there are two main types of stems cells: embryonic stem cells and adult stem cells. In a developing embryo stem cells differentiate into all types of cells, thereby creating specialized tissues, organs, and systems. In an adult human, stem cells are involved in the normal turnover of organs such as blood and skin.

Hematopoietic stem cells, for example, are used to treat blood and immune system diseases because they can differentiate into red blood cells, white blood cells, and platelets. However, some stem cell transplants have been performed for patients with genetic or metabolic diseases. Indeed, to date more than 80 different diseases have been treated using stem cell transplants. According to the National Cord Blood Program, there were over 15,000 through the end of 2009. The National Marrow Donor Program estimates that there will be 10,000 cord blood transplants per year by 2015, up from 2,000 per year in 2006.

In addition to known treatments involving stem cells, research continues into the promise of many potential future applications. Indeed, the ability of stem cells to differentiate into other types of cells holds significant promise for treating some of the world's most common diseases including heart disease, diabetes, stroke, hearing loss, blood disorders, Parkinson's disease, and Alzheimer's disease, just to name a few.

Umbilical cord blood—blood which remains in the placenta and umbilical cord after childbirth—is one of the most common sources of stem cells. Since cord blood is collected from the placenta, which is normally discarded, the collection process is safe for both the mother and the newborn.

Cord blood is obtained by syringing out the placenta through the umbilical cord shortly after childbirth, after the cord has been detached from the newborn. The retrieved blood can then be frozen and stored indefinitely.

Although the amount of stem cells obtained from cord blood is generally enough to treat a child, there are generally not enough stem cells to treat an adult patient. The placenta is a better source of stem cells, since it can contain up to ten times more stem cells than cord blood. Still, even when blood is retrieved from both the umbilical cord and placenta using current collection methods, the amount of stem cells is often not suitable to treat an adult patient.

As a result, there is a continued need for cord blood collection methods and devices that significantly increase the number of stem cells collected, facilitate the collection of stem cells, or allow for the collection of enough stem cells to treat at least one adult patient.

BRIEF SUMMARY OF THE INVENTION

It is therefore a principal object and advantage of the present invention to provide a method, device, and/or system for the collection of cord blood.

It is another object and advantage of the present invention to provide a method, device, and/or system to increase the number of stem cells collected from cord blood.

Other objects and advantages of the present invention will in part be obvious, and in part appear hereinafter.

According to one aspect, a method for collecting stem cells from a placenta, the method comprising the steps of: (i) draining cord blood from the placenta; (ii) collecting the drained cord blood in a first collection; (iii) perfusing the drained placenta with a first perfusion solution, the first perfusion solution comprising a placental preservative base solution and a vasodilator; (iv) perfusing the placenta with a second perfusion solution, the second perfusion solution comprising said placental preservative base solution, a stem cell releasing agent, an antibiotic, and an anticoagulant; (v) waiting for a predetermined amount of time as the first and second perfusion solutions perfuse the placenta; and (vi) collecting, in a second collection, said first and second perfusion solutions from the placenta, wherein said first and second perfusion solutions comprise stem cells from the placenta.

According to an embodiment, the vasodilator is prostaglandin such as at a concentration of approximately 2 µg/ml, the placental preservative base solution comprises NaCl, KCl, glucose, citric acid, adenine, histidine, glutamate, glutathione, and N-acetyl-L-cysteine, the stem cell releasing agent is 1, 1'-[1,4-phenylenebis (methylene)]-bis-1,4,8,11-tetraazacyclotetradecane ("Mozobil") or a pharmaceutically acceptable salt thereof, at a concentration of approximately 100 µg/ml.

According to an embodiment, the antibiotic comprises an aminoglycoside antibiotic such as gentamicin. According to an embodiment, the concentration of gentamicin in said second perfusion solution is approximately 80 µg/ml.

According to an embodiment, the anticoagulant comprises heparin, and can be present at a concentration of approximately 100 units/ml.

According to an embodiment, the second perfusion solution further comprises a vasodilator. According to an embodiment, the vasodilator is papaverine. According to an embodiment, the concentration of papaverine in said second perfusion solution is approximately 1 mg/ml.

According to an embodiment, the placental preservative base solution comprises NaCl at a concentration of approximately 4.3 g/L, KCl at a concentration of approximately 0.45 g/L, glucose at a concentration of approximately 1 g/L, citric acid at a concentration of approximately 2.8 g/L, adenine at a concentration of approximately 0.25 g/L, histidine at a concentration of approximately 4.2 g/L, glutamate at a concentration of approximately 2 g/L, glutathione at a concentration of approximately 1 g/L, and N-acetyl-L-cysteine at a concentration of approximately 0.016 g/L. According to an embodiment, the osmolarity of the placental preservative base solution is approximately 280 to 300 mOsm/kg.

According to an aspect is a method for collecting stem cells from a placenta comprising the steps of: (i) draining cord blood from the placenta; (ii) perfusing the drained placenta with a first perfusion solution, the first perfusion solution comprising a placental preservative base solution and prostaglandin; (iii) perfusing the drained placenta with a second perfusion solution, the second perfusion solution comprising said placental preservative base solution, 1, 1'-[1,4-phenylenebis (methylene)]-bis-1,4,8,11-tetraazacyclotetradecane ("Mozobil"), gentamicin, and heparin; and (iv) collecting said first and second perfusion solutions from the placenta, wherein said first and second perfusion solutions comprise stem cells from the placenta; (v) wherein the concentration of prostaglandin in said first perfusion solution is approximately 2 μg/ml, the concentration of Mozobil in said second perfusion solution is approximately 100 μg/ml, the concentration of gentamicin in said second perfusion solution is approximately 80 μg/ml, the concentration of heparin in said second perfusion solution is approximately 100 units/ml, and wherein the placental preservative base solution comprises NaCl at a concentration of approximately 4.3 g/L, KCl at a concentration of approximately 0.45 g/L, glucose at a concentration of approximately 1 g/L, citric acid at a concentration of approximately 2.8 g/L, adenine at a concentration of approximately 0.25 g/L, histidine at a concentration of approximately 4.2 g/L, glutamate at a concentration of approximately 2 g/L, glutathione at a concentration of approximately 1 g/L, and N-acetyl-L-cysteine at a concentration of approximately 0.016 g/L.

According to an aspect is a system for placental perfusion comprising: (i) a first perfusion solution, the first perfusion solution comprising a placental preservative base solution and prostaglandin; and (ii) a second perfusion solution, the second perfusion solution comprising said placental preservative base solution, 1, 1'-[1,4-phenylenebis (methylene)]-bis-1,4,8,11-tetraazacyclotetradecane ("Mozobil"), gentamicin, and heparin.

According to an embodiment, the concentration of prostaglandin in said first perfusion solution is approximately 2 μg/ml, the concentration of Mozobil in said second perfusion solution is approximately 100 μg/ml, the concentration of gentamicin in said second perfusion solution is approximately 80 μg/ml, the concentration of heparin in said second perfusion solution is approximately 100 units/ml, and wherein the placental preservative base solution comprises NaCl at a concentration of approximately 4.3 g/L, KCl at a concentration of approximately 0.45 g/L, glucose at a concentration of approximately 1 g/L, citric acid at a concentration of approximately 2.8 g/L, adenine at a concentration of approximately 0.25 g/L, histidine at a concentration of approximately 4.2 g/L, glutamate at a concentration of approximately 2 g/L, glutathione at a concentration of approximately 1 g/L, and N-acetyl-L-cysteine at a concentration of approximately 0.016 g/L.

According to an embodiment, the system comprises a cord blood collection bag configured to receive and store blood drained from the placenta, and a perfusion solution collection bag configured to receive and store said first and second perfusion solutions when drained from the placenta.

Methods and solutions for the preservation and procurement of placental stem cells. According to one aspect, a method for collecting stem cells from a placenta comprises: draining cord blood from the placenta; perfusing the drained placenta with a perfusion solution, the perfusion solution comprising a placental preservative, a stem cell releasing agent, an antibiotic, and a vasodilator; and collecting the stem cells and perfusion solution from the placenta.

In one implementation, the placental preservative comprises NaCl, KCl, glucose, citric acid, adenine, histidine, glutamate, glutathione, and N-acetyl-L-cysteine.

In one implementation, the placental preservative comprises NaCl at a concentration of approximately 4.3 g/L, KCl at a concentration of approximately 0.45 g/L, glucose at a concentration of approximately 1 g/L, citric acid at a concentration of approximately 2.2 g/L, adenine at a concentration of approximately 0.25 g/L, histidine at a concentration of approximately 4.2 g/L, glutamate at a concentration of approximately 1.9 g/L, glutathione at a concentration of approximately 0.92 g/L, and N-acetyl-L-cysteine at a concentration of approximately 0.016 g/L.

In one implementation, the placental preservative comprises approximately 125 to 150 mM $Na^+$; approximately 5 to 7 mM $K^+$; approximately 50 to 150 mM $Cl^-$; and/or approximately 280 to 300 mOsm/kg.

In one implementation, the stem cell releasing agent is 1, 1'-[1,4-phenylenebis (methylene)]-bis-1,4,8,11-tetraazacyclotetradecane or a pharmaceutically acceptable salt thereof.

In one implementation, the antibiotic comprises an aminoglycoside antibiotic including but not limited to gentamicin.

In one implementation, the vasodilator comprises papaverine. In one implementation, the papaverine is administered at a concentration of approximately 1 mg/ml.

In one implementation, the vasodilator is selected from the group consisting of nitroglycerine, a $Ca^{2+}$ channel blocker, an opium alkaloid, and combinations thereof.

In another aspect, a method for collecting stem cells from a placenta comprises: draining cord blood from the placenta; perfusing the drained placenta with a perfusion solution, the perfusion solution comprising 1, 1'-[1,4-phenylenebis (methylene)]-bis-1,4,8,11-tetraazacyclotetradecane or a pharmaceutically acceptable salt thereof, an aminoglycoside antibiotic, papaverine, and a placental preservative, the placental preservative comprising NaCl, KCl, glucose, citric acid, adenine, histidine, glutamate, glutathione, and N-acetyl-L-cysteine; and collecting the stem cells and perfusion solution from the placenta.

In one implementation, the placental preservative comprises NaCl at a concentration of approximately 4.3 g/L, KCl at a concentration of approximately 0.45 g/L, glucose at a concentration of approximately 1 g/L, citric acid at a concentration of approximately 2.2 g/L, adenine at a concentration of approximately 0.25 g/L, histidine at a concentration of approximately 4.2 g/L, glutamate at a concentration of approximately 1.9 g/L, glutathione at a concentration of approximately 0.92 g/L, and N-acetyl-L-cysteine at a concentration of approximately 0.016 g/L.

In another aspect, a placental perfusion solution comprising: a placental preservative; a stem cell releasing agent; an antibiotic; and a vasodilator.

In one implementation, the stem cell releasing agent comprises 1, 1'-[1,4-phenylenebis (methylene)]-bis-1,4,8,11-tetraazacyclotetradecane, said antibiotic comprises an aminoglycoside antibiotic, and said vasodilator comprises papaverine.

In one implementation, the placental preservative comprises NaCl, KCl, glucose, citric acid, adenine, histidine, glutamate, glutathione, and N-acetyl-L-cysteine.

In one implementation, the placental preservative NaCl at a concentration of approximately 4.3 g/L, KCl at a concentration of approximately 0.45 g/L, glucose at a concentration of approximately 1 g/L, citric acid at a concentration of approximately 2.2 g/L, adenine at a concentration of approximately 0.25 g/L, histidine at a concentration of approximately 4.2 g/L, glutamate at a concentration of approximately 1.9 g/L, glutathione at a concentration of approximately 0.92 g/L, and N-acetyl-L-cysteine at a concentration of approximately 0.016 g/L.

BRIEF DESCRIPTION OF THE SEVERAL VIEWS OF THE DRAWING(S)

Figure 2:
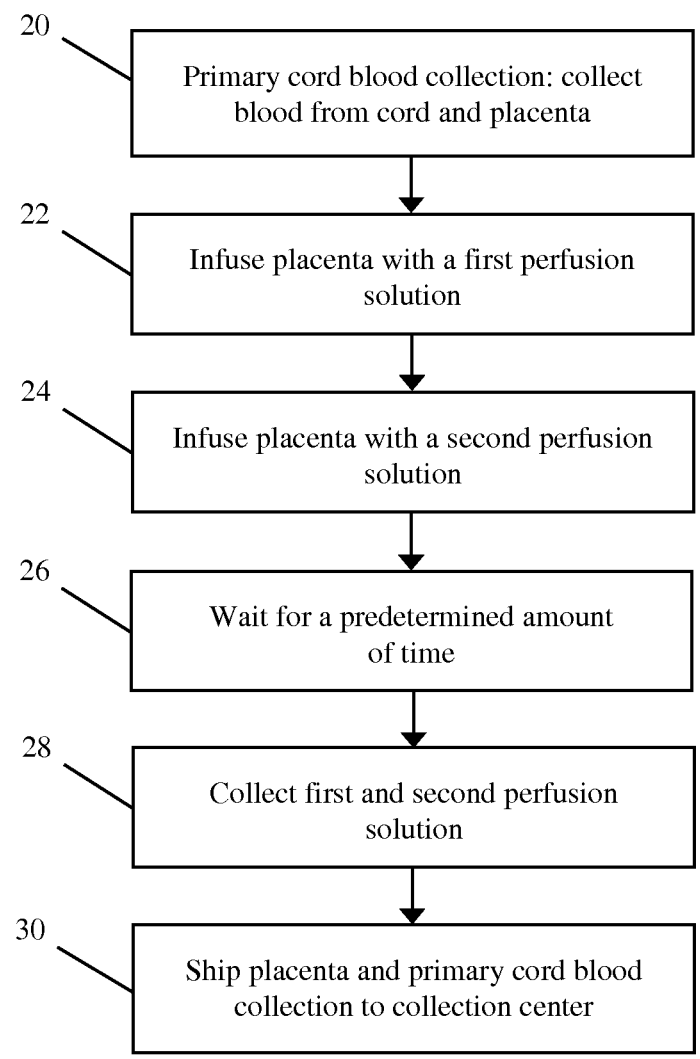

The present invention will be more fully understood and appreciated by reading the following Detailed Description in conjunction with the accompanying drawings, in which:

FIG. 1 is a flowchart of a method of stem cell collection according to an embodiment; and FIG. 2 is a flowchart of a method of stem cell collection according to an embodiment.

DETAILED DESCRIPTION OF THE INVENTION

Referring now to the drawings, wherein like reference numerals refer to like parts throughout, there is seen in FIG. 1 a flowchart of a method of stem cell collection according to one embodiment of the present invention. At step 10 is the primary cord blood collection procedure. This is accomplished using any of a variety of known cord blood collection methods, or any method capable of collecting the excess cord blood from the umbilical cord and/or placenta shortly after childbirth. For example, the cord blood can be collected using the following procedure: (i) deliver the baby vaginally or via cesarean section; (ii) clamp the umbilical cord at both the mother's and the child's side and cut the cord at a location between the clamps; (iii) insert a tube or needle into the umbilical vein to collect the blood via gravity; and (iv) ship the blood off for processing and dispose of the placenta. In a preferred embodiment, the cord blood is collected after delivery of the baby but before delivery of the placenta.

As described in the above cord blood collection method, the placenta is typically disposed and/or destroyed upon completion of the typical cord blood collection procedure. As such, these methods do not proceed past step 10 of the present method.

At step 12 of the present method, the placenta is filled with the cord blood collection solution. According to one embodiment of the present invention, the cord blood collection solution comprises the following:
i. a placental preservative base;
ii. a stem cell releasing agent;
iii. an antibiotic; and
iv. a vasodilator.

According to one embodiment of the present invention, the stem cell releasing agent can be any agent capable of causing stem cells to release from normal storage sites into the blood. According to one embodiment of the present invention, the stem cell releasing agent is AMD3100 1,1'-[1,4-Phenylenebis(methylene)]bis[1,4,8,11-tetraazacyclotetradecane] (or a pharmaceutically acceptable salt thereof), also known by the International Nonproprietary Name plexifor, by the trade name MOZOBIL®, and as JM 3100), preferably at a concentration of approximately 3-10 mg per 100 ml, although other concentrations are possible. The AMD3100 causes, among other conditions, the release of stem cells from the placenta blood vessel walls, resulting in substantially higher amounts of stem cells to be collected via the process described herein. The antibiotic can be, for example, any agent capable of providing bactericidal properties against a range of human bacterial infections, while being substantially non-toxic to humans. According to one implementation, the antibiotic is an aminoglycoside antibiotic. One such antibiotic is gentamicin, which is preferably at a concentration of approximately 10 mg per 100 ml in this embodiment, although other concentrations are possible. Lastly, the vasodilator can be any agent capable of dilating the blood vessels of the umbilical cord and placenta. One such vasodilator is papaverine, which is preferably at a concentration of approximately 100 mg per 100 ml in this embodiment, although other concentrations are possible. Other vasodilators include but are not limited to nitroglycerine, $Ca^{2+}$ channel blockers, and other opium alkaloids, for example.

The placental preservative base can be any solution capable of preserving the placenta during shipping and short- and/or long-term storage. According to one embodiment of the present invention, the placental preservative base comprises the following:
i. NaCl (4.3 g/L or 74 mM);
ii. KCl (0.45 g/L or 6 mM);
iii. D-glucose (1 g/L or 5.6 mM);
iv. citric acid anhydrous (2.2 g/L or 15 mM);
v. adenine free base (0.25 g/L or 1.85 mM);
vi. histidine (4.2 g/L or 20 mM);
vii. glutamate (1.9 g/L or 13 mM)
viii. glutathione (0.92 g/L or 3 mM; and
ix. N-acetyl-L-cysteine (also known as acetylcysteine or N-acetylcysteine) (0.016 g/L or 0.1 mM).

Although a preferred concentration is provided, one of ordinary skill in the art would recognize that one or more of the above concentrations can be varied without affecting the effectiveness or activity of the placental preservative base. Further, one of ordinary skill in the art would recognize that one or more of the above components can be omitted or replaced depending on a variety of factors. According to one embodiment, the target electrolyte and glucose profile of the placental preservative base comprises: (i) approximately 0 to 250 mM $Na^+$, with a preferred embodiment comprising approximately 125 to 150 mM $Na^+$; (ii) approximately 0 to 25 mM $K^+$, with a preferred embodiment comprising approximately 5 to 7 mM $K^+$; (iii) approximately 0 to 250 mM $Cl^-$, with a preferred embodiment comprising approximately 50 to 150 mM $Cl^-$; (iv) 0 to 10 mM glucose, with a preferred embodiment comprising approximately 5 mM glucose; (v) and osmolarity of 100 to 400 mOsm/kg, with a preferred embodiment comprising approximately 280 to 300 mOsm/kg.

In a preferred embodiment, the cord blood collection solution is allowed to fill the placenta via gravity through a needle or tube inserted into the umbilical vein and/or other locations in the placenta. Once the placenta contains a sufficient amount of cord blood collection solution, decided by a variety of factors including the predetermined amount of solution provided for collection, the size of the placenta, and/or prescribed collection procedure, among many others, the umbilical cord is once again clamped shut such that the injected solution remains inside the placenta.

Once the placenta has been refilled with the cord blood collection solution at step 12, the placenta is processed for shipping to a processing/collection center. This can include, among other things, processing the umbilical cord to ensure clamping, placing the placenta in a container suitable for short- or long-term shipping or storage, and/or freezing the placenta. Together with the primary cord blood collection, the placenta is then shipped or delivered to the processing/collection center. At some locations, the processing/collection center may be the same institution or near the same institution as the baby delivery center.

At step 16, the placenta undergoes processing at the processing/collection center. The cord blood collection solution is collected from the placenta at this step. This "secondary collection" is then processed to concentrate the mononuclear cell content and is then cryogenically stored together, but in separate containers, with the primary cord collection. The two collections may or may not be combined prior to storage depending upon a variety of factors, including but not limited to storage limitations and known or possible future uses of the stem cells, among others. The placenta can be cryogenically stored as well, or can be disposed of once the procedure is complete. In a preferred embodiment, the cord blood collection solution is allowed to drain from the placenta via gravity through a needle or tube inserted into the umbilical vein and/or other locations in the placenta. To begin draining, the umbilical cord is unclamped to allow the egress of fluid, and any drained fluid is then collected.

In yet another embodiment, the placenta is cryogenically stored prior to the secondary collection. In this embodiment, the injected cord blood collection solution is stored inside the placenta until it is needed, or until it can be more properly processed.

According to another embodiment, the collection process comprises two separate perfusion solutions that are combined in the placenta and then collected. There is seen in FIG. 2 a flowchart of a method of stem cell collection according to an embodiment. At step 20 is the primary cord blood collection procedure. This is accomplished using any of a variety of known cord blood collection methods, or any method capable of collecting the excess cord blood from the umbilical cord and/or placenta shortly after childbirth. For example, the cord blood can be collected using the following procedure: (i) deliver the baby vaginally or via cesarean section; (ii) clamp the umbilical cord at both the mother's and the child's side and cut the cord at a location between the clamps; (iii) deliver the placenta; (iv) insert a tube or needle into the umbilical vein to collect the blood; and (v) ship the blood off for processing and dispose of the placenta. In one embodiment, the cord blood is collected after delivery of the baby but before delivery of the placenta. As another example, the placenta is delivered, dried, placed in a storage or collection envelope, placed on a collection stand, and the blood is collected using standard collection methods. The sample can be collected in a bag containing anticoagulant, and this primary bag can be clamped and sealed for storage, shipping, or other processing. The placenta is typically disposed of and/or destroyed upon completion of the typical cord blood collection procedure. However, for the methods described herein, the placenta is maintained for continued processing/collection after this initial collection.

At step 22 of the flowchart in FIG. 2, the drained placenta is filled with a first perfusion solution. According to a preferred embodiment, the placenta is slowly injected with approximately 10 mls of the first perfusion solution, although this amount may vary depending upon the particular protocol or the size of the placenta. In a preferred embodiment, the first perfusion solution is allowed to fill the placenta via gravity through a needle or tube inserted into the umbilical vein and/or other locations in the placenta. According to one embodiment of the present invention, the first perfusion solution comprises a placental preservative base and a vasodilator. Lastly, the vasodilator can be any agent capable of dilating the blood vessels of the umbilical cord and placenta. According to a preferred embodiment, the vasodilator is prostaglandin, and the concentration of the prostaglandin is approximately 2 µg/ml. Another vasodilator is papaverine, which is preferably at a concentration of approximately 100 mg per 100 ml in this embodiment, although other concentrations are possible. Other vasodilators include but are not limited to nitroglycerine, $Ca^{2+}$ channel blockers, and other opium alkaloids, for example.

According to an embodiment, the placental preservative base can be any solution capable of preserving the placenta during shipping and short- and/or long-term storage, or collecting cells from the placenta. According to one embodiment of the present invention, the placental preservative base comprises approximately the following:
  i. NaCl (4.3 g/L or 74 mM);
  ii. KCl (0.45 g/L or 6 mM);
  iii. D-glucose (1 g/L or 5.6 mM);
  iv. citric acid anhydrous (2.2 g/L or 15 mM);
  v. adenine free base (0.25 g/L or 1.85 mM);
  vi. histidine (4.2 g/L or 20 mM);
  vii. glutamate (1.9 g/L or 13.3 mM)
  viii. glutathione (0.92 g/L or 3 mM; and
  ix. N-acetyl-L-cysteine (also known as acetylcysteine or N-acetylcysteine) (0.016 g/L or 0.1 mM).

Although a preferred concentration is provided, one of ordinary skill in the art would recognize that one or more of the above concentrations can be varied without affecting the effectiveness or activity of the placental preservative base. Further, one of ordinary skill in the art would recognize that one or more of the above components can be omitted or replaced depending on a variety of factors. According to one embodiment, the target electrolyte and glucose profile of the placental preservative base comprises: (i) approximately 0 to 250 mM $Na^+$, with a preferred embodiment comprising approximately 130 to 140 mM $Na^+$; (ii) approximately 0 to 25 mM $K^+$, with a preferred embodiment comprising approximately 5 to 7 mM $K^+$; (iii) approximately 0 to 250 mM $Cl^-$, with a preferred embodiment comprising approximately 100 mM Cr; (iv) 0 to 10 mM glucose, with a preferred embodiment comprising approximately 5.5 mM glucose; (v) and osmolarity of 100 to 400 mOsm/kg, with a preferred embodiment comprising approximately 280 to 300 mOsm/kg.

At step 24, the placenta is filled with a second perfusion solution. According to a preferred embodiment, the placenta is slowly injected with approximately 50 mls of the second perfusion solution, although this amount may vary depending upon the particular protocol or the size of the placenta. In a preferred embodiment, the perfusion solution is allowed to fill the placenta via gravity through a needle or tube inserted into the umbilical vein and/or other locations in the placenta. According to one embodiment of the present invention, the second perfusion solution comprises a placental preservative base and one or more of: (i) the placental preservative base; (ii) a stem cell releasing agent; (iii) an antibiotic; and (iv) an anticoagulant. Surprisingly, the steps of a first and second perfusion significantly increases the amount of stem cells retrieved from the system, which greatly increases the usefulness of the procedure and the collection.

According to one embodiment, the stem cell releasing agent in the second perfusion solution can be any agent capable of causing stem cells to release from normal storage sites into the blood/solution(s). According to one embodiment of the present invention, the stem cell releasing agent is AMD3100 1,1'-[1,4-Phenylenebis(methylene)]bis[1,4,8, 11-tetraazacyclotetradecane] (or a pharmaceutically acceptable salt thereof), also known by the International Nonproprietary Name plexifor, by the trade name MOZOBIL®, and as JM 3100), preferably at a concentration of approximately 100 µg/ml, although other concentrations are possible. The AMD3100 causes, among other conditions, the release of stem cells from the placenta blood vessel walls, resulting in substantially higher amounts of stem cells to be collected via the process described herein.

According to one embodiment, the antibiotic can be, for example, any agent capable of providing bactericidal properties against a range of human bacterial infections, while being substantially non-toxic to humans. According to one implementation, the antibiotic is an aminoglycoside antibiotic. One such antibiotic is gentamicin, which can be at a concentration of approximately 80 µg/ml, although other concentrations are possible.

According to one embodiment, the anticoagulant can be, for example, any anticoagulant capable of preventing coagulation. According to a preferred embodiment, the anticoagulant is heparin at a concentration of approximately 100 units per ml, although other concentrations are possible. Many other anticoagulants are possible.

At step 26, the first and second perfusion solutions are allowed to dwell within the placenta for a predetermined period of time. According to an embodiment, the predetermined amount of time is 3-5 minutes, although other dwell times are possible. For example, according to one embodiment, the placenta can be shipped to a processing/collection center containing the first and second perfusion solutions.

At step 28 of the method depicted in FIG. 2, the first and second perfusion solutions are collected from the placenta. This "secondary collection" is collected in an appropriate bag/container for shipping and/or storage. The secondary collection can be performed using a gravity-based collection, or the placenta can be manipulated to promote collection, among other collection methods. The primary and secondary collections can be cryogenically stored together, in the same or separate containers. The two collections may or may not be combined prior to storage depending upon a variety of factors, including but not limited to storage limitations and known or possible future uses of the stem cells, among others. The placenta can be cryogenically stored as well, or can be disposed of once the procedure is complete. In a preferred embodiment, the solutions are allowed to drain from the placenta via gravity through a needle or tube inserted into the umbilical vein and/or other locations in the placenta. To begin draining, the umbilical cord is unclamped to allow the egress of fluid, and any drained fluid is then collected.

At step 30, the placenta and/or two collections are processed and stored or shipped to a processing or storage center. This can include, among other things, processing the umbilical cord to ensure clamping, placing the placenta in a container suitable for short- or long-term shipping or storage, and/or freezing the placenta. Together with the collection, the placenta is then shipped or delivered to the processing/collection center. At some locations, the processing/collection center may be the same institution or near the same institution as the baby delivery center.

Although the present invention has been described in connection with a preferred embodiment, it should be understood that modifications, alterations, and additions can be made to the invention without departing from the scope of the invention as defined by the claims.

What is claimed is:

1. A method for collecting stem cells from a placenta obtained after childbirth, the method comprising:
    draining cord blood from the placenta obtained after childbirth;
    collecting the drained cord blood in a first collection;
    infusing the drained placenta with a first solution, the first solution consisting of a placental preservative base solution and prostaglandin, wherein the placental preservative base solution consists of NaCl, KCl, glucose, citric acid, adenine, histidine, glutamate, glutathione, and N-acetyl-L-cysteine;
    infusing the placenta with a second solution before the first solution is collected, the second solution consisting of said placental preservative base solution, a stem cell releasing agent, an antibiotic, and an anticoagulant, wherein the stem cell releasing agent is 1, 1'-[1,4-phenylenebis (methylene)]-bis-1,4,8,11-tetraazacyclotetradecane or a pharmaceutically acceptable salt thereof;
    waiting for a predetermined amount of time as the first and second solutions perfuse the placenta, wherein said predetermined amount of time is 5 minutes or fewer; and
    collecting, in a second collection, said first and second solutions from the placenta, wherein the collected first and second solutions comprise stem cells from the placenta.

2. The method of claim 1, wherein the concentration of prostaglandin in said first solution is approximately 2 µg/ml.

3. The method of claim 1, wherein the concentration of 1, 1'-[1,4,-phenylenebis (methylene)]-bis-1,4,8,11-tetraazacyclotetradecane in said second solution is approximately 100 µg/ml.

4. The method of claim 1, wherein the antibiotic is an aminoglycoside antibiotic.

5. The method of claim 4, wherein the antibiotic is gentamicin.

6. The method of claim 5, wherein the concentration of gentamicin in said second solution is approximately 80 µg/ml.

7. The method of claim 1, wherein the anticoagulant is heparin.

8. The method of claim 7, wherein the concentration of heparin in said second solution is approximately 100 units/ml.

9. The method of claim 1, wherein said placental preservative base solution consists of NaCl at a concentration of approximately 4.3 g/L, KCl at a concentration of approximately 0.45 g/L, glucose at a concentration of approximately 1 g/L, citric acid at a concentration of approximately 2.8 g/L, adenine at a concentration of approximately 0.25 g/L, histidine at a concentration of approximately 4.2 g/L, glutamate at a concentration of approximately 2 g/L, glutathione at a concentration of approximately 1 g/L, and N-acetyl-L-cysteine at a concentration of approximately 0.016 g/L.

10. The method of claim 1, wherein the osmolarity of the placental preservative base solution is approximately 280 to 300 mOsm/kg.

11. A method for collecting stem cells from a placenta obtained after childbirth, the method comprising:
    draining cord blood from the placenta obtained after childbirth;
    infusing the drained placenta with a first solution, the first solution consisting of a placental preservative base solution and prostaglandin;
    infusing the drained placenta with a second solution before the first solution is collected, the second solution consisting of said placental preservative base solution, 1, 1'-[1,4-phenylenebis (methylene)]-bis-1,4,8,11-tetraazacyclotetradecane, gentamicin, and heparin;

waiting for a predetermined amount of time as the first and second solutions perfuse the placenta, wherein said predetermined amount of time is 5 minutes or fewer; and collecting said first and second solutions from the placenta, wherein the collected first and second solutions comprise stem cells from the placenta;

wherein the concentration of prostaglandin in said first solution is approximately 2 μg/ml, the concentration of Mozobil in said second solution is approximately 100 μg/ml, the concentration of gentamicin in said second solution is approximately 80 μg/ml, the concentration of heparin in said second solution is approximately 100 units/ml, and wherein the placental preservative base solution consists of NaCl at a concentration of approximately 4.3 g/L, KCl at a concentration of approximately 0.45 g/L, glucose at a concentration of approximately 1 g/L, citric acid at a concentration of approximately 2.8 g/L, adenine at a concentration of approximately 0.25 g/L, histidine at a concentration of approximately 4.2 g/L, glutamate at a concentration of approximately 2 g/L, glutathione at a concentration of approximately 1 g/L, and N-acetyl-L-cysteine at a concentration of approximately 0.016 g/L.

12. A method for collecting stem cells from a placenta obtained after childbirth, the method comprising:

draining cord blood from the placenta obtained after childbirth;

collecting the drained cord blood in a first collection;

infusing the drained placenta with a first solution, the first solution consisting of a placental preservative base solution and prostaglandin, wherein the placental preservative base solution consists of NaCl, KCl, glucose, citric acid, adenine, histidine, glutamate, glutathione, and N-acetyl-L-cysteine;

infusing the placenta with a second solution before the first solution is collected, the second solution consisting of said placental preservative base solution, a stem cell releasing agent, an antibiotic, a vasodilator, and an anticoagulant, wherein the stem cell releasing agent is 1, 1'-[1,4-phenylenebis (methylene)]bis-1,4,8,11-tetraazacyclotetradecane or a pharmaceutically acceptable salt thereof;

waiting for a predetermined amount of time as the first and second solutions perfuse the placenta, wherein said predetermined amount of time is 5 minutes or fewer; and collecting, in a second collection, said first and second solutions from the placenta, wherein the collected first and second solutions comprise stem cells from the placenta.

13. The method of claim 12, wherein the vasodilator is papaverine.

14. The method of claim 13, wherein the concentration of papaverine in said second solution is approximately 1 mg/ml.

* * * * *